(12) United States Patent
Simons (10) Patent No.: US 12,073,940 B2
(45) Date of Patent: Aug. 27, 2024

(54) EXTRACTING SALES AND UPGRADE OPPORTUNITIES FROM UTILIZATION DATA

(71) Applicant: KONINKLIJKE PHILIPS N.V., Eindhoven (NL)

(72) Inventor: Paul Richard Simons, Cambridge (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 635 days.

(21) Appl. No.: 16/758,073

(22) PCT Filed: Oct. 22, 2018

(86) PCT No.: PCT/EP2018/078837
§ 371 (c)(1),
(2) Date: Apr. 22, 2020

(87) PCT Pub. No.: WO2019/081399
PCT Pub. Date: May 2, 2019

(65) Prior Publication Data
US 2020/0365261 A1   Nov. 19, 2020

Related U.S. Application Data

(60) Provisional application No. 62/576,727, filed on Oct. 25, 2017.

(51) Int. Cl.
*G16H 40/40* (2018.01)
*G06F 21/62* (2013.01)
(Continued)

(52) U.S. Cl.
CPC ......... *G16H 40/40* (2018.01); *G06F 21/6254* (2013.01); *G06N 20/00* (2019.01);
(Continued)

(58) Field of Classification Search
CPC ........ G16H 40/40; G16H 40/20; G16H 50/20; G06F 21/6254; G06N 20/00;
(Continued)

(56) References Cited

U.S. PATENT DOCUMENTS 10,360,601 B1 *   7/2019   Adegan .............. G06Q 30/0283
2002/0082864 A1   6/2002   Kelley
(Continued)

FOREIGN PATENT DOCUMENTS

| JP | 2002345802 A | 12/2002 |
| JP | 2003216729 A | 7/2003 |
| JP | 4333084 B2 * | 9/2009 ........... G06F 3/1204 |

OTHER PUBLICATIONS

Minassian, Veronik. Essentially smart contracts. 24x714.2: 28(3). Allied Media LLC. (Feb. 2009) (Year: 2009).*
(Continued)

*Primary Examiner* — Linh Giang Le (57) ABSTRACT

A non-transitory computer-readable medium stores instructions readable and executable by a workstation (20) including at least one electronic processor (22) to perform a method (100) for generating medical imaging device upgrade recommendations from utilization data. The method includes: retrieving, from at least one database (14), 5 utilization data (30) from logs of a plurality of installed medical imaging devices (16); applying a set of rules (29) to the utilization data to identify one or more upgrade recommendations wherein each upgrade recommendation comprises: an identification of one or more of the installed medical imaging devices or components of the installed medical imaging devices recommended to be upgraded or replaced; and at least one of a 10 replacement medical imaging device or component or a new medical imaging device or component for each of the installed medical imaging devices or components recommended to be
(Continued)

upgraded or replaced; and displaying, on a display device (26), a list (38) of the at least one identified replacement or new medical imaging device or component.

20 Claims, 5 Drawing Sheets

(51) Int. Cl.
*G06N 20/00* (2019.01)
*G06Q 10/0637* (2023.01)
*G06Q 30/0601* (2023.01)
*G16H 40/20* (2018.01)
*G16H 50/20* (2018.01)
*G06Q 10/04* (2023.01)

(52) U.S. Cl.
CPC ... *G06Q 10/06375* (2013.01); *G06Q 30/0631* (2013.01); *G16H 40/20* (2018.01); *G16H 50/20* (2018.01); *G06Q 10/04* (2013.01)

(58) Field of Classification Search
CPC ......... G06Q 10/06375; G06Q 30/0631; G06Q 10/04; G06Q 30/0283; G06Q 10/20
See application file for complete search history.

(56) References Cited

U.S. PATENT DOCUMENTS

| | | |
|---|---|---|
| 2003/0033186 A1 | 2/2003 | Kuth |
| 2005/0246189 A1 | 11/2005 | Monitzer |
| 2006/0149808 A1* | 7/2006 | Weiner .................. G16H 40/67 |
| | | 709/203 |
| 2007/0118401 A1 | 5/2007 | Mahesh |
| 2010/0292556 A1* | 11/2010 | Golden .................. G16H 40/67 |
| | | 607/31 |
| 2013/0268890 A1* | 10/2013 | Jensen .................. G06Q 10/20 |
| | | 715/810 |
| 2017/0024640 A1 | 1/2017 | Deng |
| 2017/0032296 A1 | 2/2017 | Simons |

OTHER PUBLICATIONS

International Search Report and Written Opinion Dated Jan. 8, 2019 for International Application No. PCT/EP2018/078837 Filed Oct. 22, 2018.

Hu, et al: "Informatics in Radiology: Efficiency Metrics for Imaging Device Productivity" Radiographics., vol. 31, No. 2, Mar. 1, 2011.

Glynn, et al: "Lifecycle Guidance for Medical Imaging Equipment in Canada 2013 Main Report Acknowledgements", 2013 https://car.ca/wp-content/uploads/car-1i fecyclegui dance-mai nreport.pdf.

* cited by examiner

EXTRACTING SALES AND UPGRADE OPPORTUNITIES FROM UTILIZATION DATA

CROSS REFERENCE TO RELATED APPLICATIONS

This application is the U.S. National Phase application under 35 U.S.C. § 371 of International Application No. PCT/EP2018/078837 filed Oct. 22, 2018, published as WO 2019/081399 on May 2, 2019, which claims the benefit of U.S. Provisional Patent Application No. 62/576,727 filed on Oct. 25, 2017. These applications are hereby incorporated by reference herein.

FIELD

The following relates to the medical imaging system arts, imaging system maintenance, upgrading, and sales analytics arts, and related arts.

BACKGROUND

Medical imaging systems provide tremendous medical diagnostic and clinical benefits. However, these systems are costly, and hence the cost/benefit analyses in making upgrade decisions in this area are complex. Hospital personnel tasked with upgrading these systems can be overwhelmed by the task, and as occasional purchasers of such equipment are often ill-equipped to decide whether a given system upgrade is worthwhile. They may not be familiar with the latest features and capabilities of such imaging devices. Such difficulties are increased by the rise in complexity and capabilities of modern medical imaging devices, in which a single device (possibly with certain accessories) is often capable of providing a wide range of services spanning across medical specialties and across clinical departments. For example, a single imaging device may be usable for oncology and cardiology, and perhaps other specialties. This increases the difficulty in assessing the overall value of an available upgrade to the hospital as a whole.

On the other hand, sales personnel employed by medical imaging system vendors may have greater knowledge of the latest features and capabilities of medical imaging systems currently on the market. However, they also may have limited familiarity with the day-to-day clinical practice at the hospital (i.e. target customer), and are usually not physicians or other qualified clinicians. Thus, while a sales person may be familiar with the capabilities of a certain product offering, the sales person may struggle to contextualize and articulate its value within the day-to-day working environment of the hospital.

Accordingly, opportunities to beneficially upgrade medical imaging equipment may be missed. This can adversely impact the vendor by way of lost sales; the hospital (or other medical institution) by way of reduced or lost medical service fees; and patients by way of being provided with non-optimal medical imaging services, or not being offered a medical imaging service that could have been beneficial to the patient.

The following discloses new and improved systems and methods to overcome these and other problems.

SUMMARY

In one disclosed aspect, a non-transitory computer-readable medium stores instructions readable and executable by a workstation including at least one electronic processor to perform a method for generating medical imaging device upgrade recommendations from utilization data. The method includes: retrieving, from at least one database, utilization data from logs of a plurality of installed medical imaging devices; applying a set of rules to the utilization data to identify one or more upgrade recommendations wherein each upgrade recommendation comprises: an identification of one or more of the installed medical imaging devices or components of the installed medical imaging devices recommended to be upgraded or replaced; and at least one of a replacement medical imaging device or component or a new medical imaging device or component for each of the installed medical imaging devices or components recommended to be upgraded or replaced; and displaying, on a display device, a list of the at least one identified replacement or new medical imaging device or component.

In another disclosed aspect, a system is configured to generate medical imaging device upgrade recommendations from utilization data. The system includes at least one electronic processor programmed to: retrieve, from at least one database, utilization data from logs of a plurality of installed medical imaging devices; apply a set of rules to the utilization data to identify one or more upgrade recommendations wherein each upgrade recommendation comprises: an identification of one or more of the installed medical imaging devices or components of the installed medical imaging devices recommended to be upgraded or replaced; and at least one of a replacement medical imaging device or component or a new medical imaging device or component for each of the installed medical imaging devices or components recommended to be upgraded or replaced. A display device is configured to display a list of the at least one identified replacement or new medical imaging device or component.

In another disclosed aspect, a non-transitory computer-readable medium stores instructions readable and executable by a workstation including at least one electronic processor to perform a method for generating medical imaging device upgrade recommendations from utilization data. The method includes: retrieving, from at least one database, utilization data from logs of a plurality of installed medical imaging devices; applying a set of rules to the utilization data to identify one or more upgrade recommendations wherein each upgrade recommendation comprises: an identification of one or more of the installed medical imaging devices or components of the installed medical imaging devices recommended to be upgraded or replaced; and at least one of a replacement medical imaging device or component or a new medical imaging device or component for each of the installed medical imaging devices or components recommended to be upgraded or replaced; and displaying, on a display device, a list of the at least one identified replacement or new medical imaging device or component by operations including: generating a natural language expression representing each upgrade recommendation wherein the natural language expression includes identification of the one or more installed medical imaging devices or components recommended to be upgraded or replaced and of the at least one identified replacement or new medical imaging device, and a summary of utilization data on which the upgrade recommendation is based; filling in fields of the natural language expression template with the identification of the one or more installed medical imaging devices or components recommended to be upgraded or replaced, the at least one identified replacement or new medical imaging device, and the summary of utilization data on which the upgrade recommendation is based; and displaying the natural language expression representing each upgrade recommendation. The summary of utilization data on which the upgrade recommendation is based includes at least one of: an increased revenue case indicating a cost of upgrade compared with a higher throughput compared with the installed medical imaging device; an additional services case indicating that the upgrade enables additional procedures not currently available with the installed medical imaging device or component; and a medical case indicated images showing an improved resolution attainable with the upgrade compared with the installed medical imaging device or component.

One advantage resides in providing systems and methods of automated creation of a medical imaging systems upgrade strategy from available information, including information derived from machine utilization data.

Another advantage resides in providing systems and methods to improve medical imaging device/accessories upgrade opportunities presented, including client: contract information, utilization information, budget information, a location of departments on site layout, new system requirements, and benefits in changing imaging systems.

Another advantage resides in providing a system to provide an imaging system upgrade opportunity articulated to a client based on the client's historical imaging device utilization data.

Another advantage resides in providing an imaging system sales opportunity or an imaging system equipment upgrade opportunity with an optimized financial model to suit a client based on the client's own data.

Another advantage resides in linking imaging systems sale selection with patient outcomes.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

In recent years, services for hosting medical imaging machine log data have been provided by medical imaging device vendors to medical imaging device customers (e.g. hospitals and other medical institutions). This facilitates rapid response to machine problems and eliminates the need for the customer's information technology (IT) department to host the machine logs (which may employ non-intuitive and/or proprietary data formatting) on local servers, which is expensive in terms of storage, maintenance, and backup.

The following discloses leveraging the utilization data from these machine logs for detecting opportunities for upgrading the existing imaging machine install base of a customer. Such an upgrade is a sales opportunity or an imaging system equipment upgrade opportunity for the vendor, and where warranted such an upgrade also benefits the customer through improved revenue and/or the ability to provide additional imaging services, and/or benefits patients by providing improved diagnostic capability and/or shorter/more productive imaging sessions. Advantageously, the utilization data is generally scrubbed of personally identifying information (PII) and hence can be used without creating HIPAA or other patient privacy issues.

In embodiments disclosed herein, a set of rules is applied to identify imaging device upgrades that provide articulable benefits for the customer and/or patients. In the illustrative approach, each existing device of the install base is represented by a spreadsheet storing the machine type and purchased peripherals, software suites, or other accessories, along with information such as the in-service date. This is augmented by data on the device extracted from the machine logs, such as the efficiency (percentage of workday actually used), number of scans performed per month, and details on these scans such as the peripherals and software tools used (from which the clinical task may be deduced), anatomy, scan type, and so forth. The log data also includes service call logs permitting detection of recurrent problems with the existing machine. To capture information on possible replacements, each machine currently offered for sale by the vendor is represented by a generic spreadsheet which identifies the machine type and all available peripherals, software, or other accessories (more generally, "components") usable with it. Optionally, such generic spreadsheets may also be created for available used imaging systems, and optionally also for competitors' imaging systems. The rules then identify possible replacement machines and/or newly added machines or components that may solve problems identified from the utilization data.

Preferably, the output of a rule indicating an upgrade opportunity is expressed in natural language format, preferably using the customer's own data (derived from the machine logs) to express a business case for the upgrade. In cases where the business case is increased revenue for the hospital, this may be expressed in terms of cost of replacement compared with higher throughput-revenue balancing. In cases where the business case is additional services capability, the benefit may for example be expressed as a statement that the additional peripheral (for example) will enable performing studies under a Current Procedural Terminology (CPT) code that is not currently billable with the existing imaging device. In cases where the business case is purely medical (e.g., for a MRI machine improved imaging resolution using a knee coil) the benefit may be expressed using images showing the improved resolution attainable with the knee coil together with statistics drawn from the machine log data showing how many examinations per month would benefit from the knee coil. Thus, the disclosed approaches provide the customer decision-maker (e.g. clinical department head, procurement officer, or other authorized purchasing agent) with tools for making the business case for the upgrade.

The spreadsheets and rules database can be primarily manually created, for example as part of the new product development process. The rules may include machine learned weights, for example trained on actual sales data or the like.

The following is applicable to any imaging or image-guided therapy (iGT) system, and upgrade opportunities may include new machines or new components (e.g., new peripherals, or new software) to identify imaging device upgrade opportunities, with benefits to the manufacturer, customer, and patients. As the disclosed approaches for identifying equipment upgrade opportunities leverage machine log data available to the imaging equipment vendor, these upgrade opportunities may be seen as sales opportunities from the viewpoint of the imaging equipment vendor, and these terms ("upgrade opportunities" and "sales opportunities") are used interchangeably herein. It will be appreciated that such a sales or upgrade opportunity is based on historical imaging machine utilization data of the customer, and hence also presents an articulable well-defined opportunity to benefit the customer and/or patients serviced by the customer.

The following discloses a method of automatically extracting sales opportunities or imaging system equipment upgrade opportunities from a database of information and providing the results to sales staff. The database comprises, for example, the system specification, contract, pricing, and utilization of each medical imaging system of interest. Information is also provided about alternative or possible replacement equipment and their comparable operational performance of old and new models.

In some embodiments, the disclosed systems and methods process each machine available for sale in turn and apply a set of sales strategies and evaluate a score to represent the likelihood of a sale for each available machine or individual recycled machines. The results are compared to a threshold, and/or are ranked or ordered allowing the system to display the best sales opportunities or imaging system equipment upgrade opportunities to the user. The results of the sales opportunities or imaging system equipment upgrade opportunities displayed are likely to be persuasive to the customer as it is derived and supported and can be directly linked for display by the corresponding customer's own utilization evidence and financial arguments that we used to evaluate a high chance of success.

In embodiments disclosed herein, a sales opportunity or an imaging system equipment upgrade opportunity can include recommending a suitable additional machine specification. Typically, sales opportunities of a new or replacement machine are preferred over an upgrade opportunity of replacement parts, as long as the new or replacement machine is within a budget. In other embodiments disclosed herein, the sales opportunity or imaging system equipment upgrade opportunity can include an additional system or a replacement system. For example, the opportunity may including purchasing a replacement machine to replace an older model if a tradeoff of cost constraints and functionality between the two is a substantially in favor of a new machine. Therefore, the rules are extended to identify the best machine type and specification that can be used to support the client (i.e. customer). Alternately, the rule may also investigate machines that can operate faster, such that client throughput can be increased and justify a replacement machine. In this case, one rule would output two opportunities, one that articulates benefits of an additional machine and another articulates benefits of a replacement machine.

Information sources used to create sales opportunities or imaging system equipment upgrade opportunities may include, but are not limited to: specification and complete costs for each existing client device, including benchmark scanning time for each main operation mode (e.g. Vascular, Obstetrics scans etc.); specification and complete costs for each device in the sales portfolio, including benchmark scamming time for each main operation mode (e.g. Vascular, Obstetrics scans etc.); estimated client budget, including increases or decreases to the current spend; contract information for each client device, including responsible internal department, machine age, payment model and replacement date; and machine utilization metrics and charts derived from existing client devices.

The rules are preferably created together with sales professionals to identify possible sales opportunities or imaging system equipment upgrade opportunities. Each rule determines a set of challenges from available recorded data associated with a machine, where for example the opportunity can be recommended based on at least one of: how close the total cost of the replacement system (including the pay-per-use price) matches the available or predicted budget of the client; patient throughput (e.g., speed and efficiency improvements associated with the new equipment, calculated using the profiling information to estimate of (improvement in) scan time based on a profile of scans derived from the existing usage statistics); new software or hardware features (e.g., suggested replacement machine enable operation modes or new connection to new peripherals that benefits the client); improvement in system performance benefits (e.g., including the differences in features (e.g. new features, image resolution, or new peripherals) between the existing system and replacement system); procurement of suggested additional or replacement machine (e.g., needed to meet demand in department) in which specific specifications are recommended based on current utilization with a detailed cost associated therewith; procurement of additional (and/or) replacement mobile machine is needed to meet demand in hospital (e.g., where the device can be time-shared between specified departments, recommend specific specification based on current utilization, whose cost is detailed); and procurement of a new or replacement machine based on comparable efficiency of current competitor install system based on benchmark figures (e.g., when no customer utilization data is available).

A wide variety of additional rules can also be defined in collaboration with sales staff, medical personnel, or other knowledge resources, to create a rule-base that considers the case for a wide variety of procurement opportunities. This enables a process to run each rule against every client machine that is in the client's facility. In addition the sales rules can compile associated information, including metrics and charts into a logical statement that is supported by a persuasive rationale for the proposed upgrade that is supported by the utilization data. A software tool such as a tablet, cellphone or other mobile app, a program running on a desktop computer, or the like can be provided to enable customer visits to prepared with several articulable sales pitches. The software can store and present different opportunity statements for each machine, looking at different upgrade opportunities based on its rule base and pulling in corresponding data associated with machine utilization, age, contract and comparisons with other systems to evaluate a score for each opportunity.

In order to facilitate a program that can identify sales opportunities or imaging system equipment upgrade opportunities, a suitable mechanism is provided for a computer to compare the specifications of different systems and to be able to select elements of a system and price a system for a customer. The machine specifications can be stored in a spread sheet that specifies all the configuration options and associated pricing of each component. These components may include application software, hardware and/or software for implementing various imaging modes and/or optimizing controls, various peripherals and services, or so forth. The spread sheet may be further extended to include a feature set of technical parameters that allow different models to be compared in terms of resolution, speed and accuracy. Further metrics can also be added that indicate average performance numbers that indicate average study times with patients across a range of different operation modes (e.g. vascular, cardiac scan times etc.). These spread sheets are integral to the software used to compare systems, where each existing system is provided with a spread sheet containing the exact specification and pricing of each component, that can be summed to a total system cost.

Each existing system of the customer's site or department (generally, "install base") is considered a candidate for the identifying sales opportunities or imaging system equipment upgrade opportunities. As such a spread sheet is configured to represent each component of the system, together with its pricing, which was normally created when the device was originally sold. Competitor products can optionally be similarly represented by a generic spreadsheet with equivalent components that are selected and an estimated price added to allow these systems also to be considered for replacement. In some examples, customer discounts can factor into a sales offer price.

Each model available for sale is also represented by a generic spread sheet that includes its own components, pricing and performance metrics, however, unlike the existing systems, no components are selected. It should be noted that this should also include the generic type of the existing system, which allows the program to consider selling software modes and/or peripherals that is not part of the existing system. Also note that models available for sale could in some embodiments, also include used machines, whose pricing will reflect the used condition and age of the machine. One illustrative embodiment described herein goes through the process of using each existing machine's specification and using it to create a sales opportunity or an imaging system equipment upgrade opportunity by configuring all the possible replacement machines to an equivalent specification and determining a related score to determine the suitability of each opportunity.

The ability to rank sales opportunities or imaging system equipment upgrade opportunities accurately facilitates identification of upgrade opportunities that are strong and trusted by the sales staff. As such they should reflect the likelihood of achieving a sale. Failing to meet a mandatory requirement is therefore preferably a basis for rejection of a candidate sales opportunity or imaging system equipment upgrade opportunity. More generally, a sliding scale may be used to analyze preferred or optional requirements to allow sales opportunities or imaging system equipment upgrade opportunities to be presented that have unmet needs, although their score will be reduced with each unmet need identified. This causes the opportunities with all needs met to rise to the top in the ranking when their likelihood scores are sorted in order. Other factors that could also be used to affect likelihood scoring are: profit earned; replacement of competitor product; and sale of a preferred model, due to stock control, or availability.

All these factors can be combined to achieve an overall score for each opportunity. As a final stage a weighting can be applied to the type of opportunity. The scores of the sales opportunities or imaging system equipment upgrade opportunities are then compared to a threshold to remove low likelihood opportunities and sorted in order for display to the sales representative.

Successful sales created as a result of opportunities presented by this tool can be used as feedback to strengthen the weighting associated with successful rules to ensure continuous improvement of the sales tool. For example: an initial rule could be set that an ultrasound device used for cardiac scanning is ideally replaced by a similar device, with high confidence and the weighting can be adapted based on its success rate of achieving sales.

In some embodiments disclosed herein, the requirements of a department, or hospital, or even organization as whole, can be considered based on the profile of existing usage. Also rules can be run for a department or a hospital (including the ability to time-share a portable machine or a non-portable machine by moving its location from one department to another). The disclosed upgrade opportunity recommendation tool could also improve this aspect by accounting for the portability of certain machines and combining this information with knowledge of the layout of a client hospital. This would allow the tool to understand whether a given machine can be shared between two departments, by understanding how far two departments are apart, and whether the machine can be easily transported between the departments, or whether the moving distance, physical and mobility will prevent this machine from being moved. For example, a large machine on wheels could be transported up a lift to another department, but not pushed across a car port to another building, whereas a portable, laptop like device can be shared between buildings. In another example, the system can be used a hospital layout to effectively use equipment, particularly if sharing equipment between multiple departments would be efficient.

The requirements for a machine or set of machines can also be based a predicted profile that might be based on other similar systems, department or hospitals. The upgrade opportunity recommendation tool is designed to identify best combinations of systems to meet all the requirements. A wide variety of combinations can be scored and combined, compared to the threshold and ranked to determine on the best match between the requirements and the available systems for sale.

The disclosed tool could also be tailored to find a replacement machine(s) for a department of a hospital taking into account additional requirements, including a specific available budget for a replacement machine(s), or for a department, hospital etc., a certain numbers of fixed, portable or static machines, a physical layout of client departments, a certain number of machines for each department, specific hardware (e.g. new vascular transducers available on new the model etc.), software modes (e.g. new 3D color imaging etc.), and specific types of machines (e.g. ultrasound, magnetic resonance imaging (MRI), positron emission tomography (PET), computed tomography (CT), X-ray etc.).

In general, sales opportunities or imaging system equipment upgrade opportunities can identified for any known install base, e.g., from a single standalone machine, for a whole department, hospital, private hospital network or even geographic region. Selection of this install base to investigate opportunities is best controlled using a customer user interface that takes into account areas of interest to sales personnel.

In another embodiment the system can enable new rules to be defined and introduced (and labelled as a prototype rule), for example to identify machines that meet the mandatory requirements provided that the pay-per-use per month cost is reduced.

In another embodiment, one or more machines can be automatically identified to best meet the requirement (for a department or hospital) of a wide variety of scans of different types (e.g. pregnancy scans, including at different development stages, kidney scans, cardiac scans etc.). Requirements may also specify costs and operational features and parameters needed by the customer. This method could be linked directly to government reimbursement rates.

In another embodiment, the systems offered to the client could be based on a range of different financial models (e.g. based on transducer usage, or scan type). Alternative sales opportunities or imaging system equipment upgrade opportunities can be created for each different financial model, where an estimate of the monthly system cost could be made based on utilization data recovered from the customer's existing machines, or predicted requirements.

In another embodiment, a sales opportunity recommendation or an imaging system equipment upgrade opportunity recommendation is linked to patient outcomes. This is possible when patient outcome data is available to process, where the use of specific machines leads to combinations of scanning, diagnosis, treatment and patient outcome that can be digitally recorded for each patient. Given the ability to process a huge amount of data, other contributing factors associated with a machine type can be eliminated. In one articulable basis for presenting such an upgrade opportunity, it may be articulated that the better the machine, the resolution of the image (and other specifications including machine features) the better the diagnosis, treatment and speed of recovery. This enables patient outcomes to be linked with machine performance and therefore to be used as a factor in machine selection. Therefore, the customer can benefit by sharing patient outcomes to be used, which will lead to better decisions of which machines are procured.

In another embodiment, the system could also be able to actively adapt based on the success of specific rule in achieving sales, or increasing profit margins. In this case, when a client agrees to replace a new machine based on a sales opportunity or an imaging system equipment upgrade opportunity, the weighting attached to the sales opportunity or the imaging system equipment upgrade opportunity is increased a little to ensure that in the future such rules have a better chance of creating sales opportunities or imaging system equipment upgrade opportunities that rise to the top and are therefore used.

Figure 1:
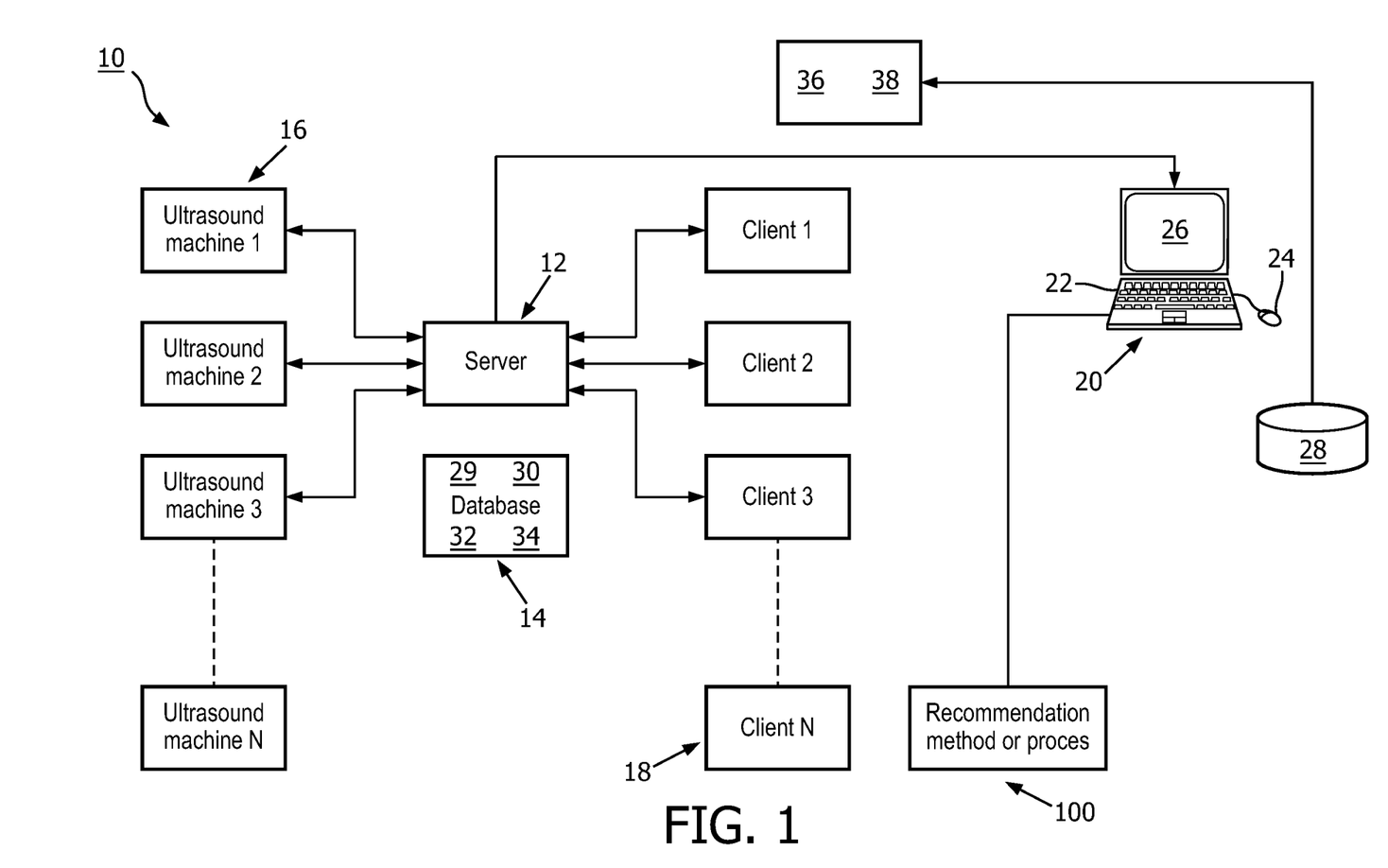
FIG. 1 diagrammatically shows a device for generating medical imaging device upgrade recommendations from utilization data according to one aspect.

With reference to FIG. 1, an illustrative imaging sales (i.e. upgrade) opportunity recommendation system 10 is shown. As shown in FIG. 1, the system 10 includes a server computer 12 (e.g., a network-based server computer, a cluster of cooperating server computers, optionally operating in an ad hoc manner, e.g. as a cloud server, or so forth) and a database 14. The system 10 is in communication with a plurality of image acquisition devices 16 (e.g., ultrasound machines) and a plurality of clients 18. The image acquisition devices 16 may be owned or leased by the clients 18, for example.

Data, such as machine logs, service logs, or so forth, may be transferred from the ultrasound machines 16 or from computers or other electronic connected to the cloud server 12 and securely stored in the database 14. For example, the server computer 12 may be hosted by the imaging devices vendor as a service to customers. (The hosting may be done directly, by having the server computer on the premises of, and owned by, the vendor; may be done indirectly by way of leasing a cloud computing resource or service from a third party to provide a "virtual" server implementing the server 12). In the normal course of operation, the client 18 may in some access this data from the server 12 as needed as part of normal operations of the client's fleet of imaging devices. Additionally or alternatively, the servicing department of the vendor may access this data from the server 12 as needed as part of normal operations in providing preventative and remedial servicing for the imaging devices under a service contract with the customer, as warranty repairs, or under some other service support arrangement between customer and vendor.

The data can also be retrieved for use by the upgrade opportunities recommendation system 10 by accessing the data from a wide variety of client devices on the cloud. The database 14 can be further augmented for such purpose with additional information, such as the specification of each device 16 and customer contract information etc. This information can subsequently be retrieved and processed on the server 12 to identify and recommend a wide range of sales opportunities or imaging system equipment upgrade opportunities. It is additionally or alternatively contemplated to allow a client 18 to use the upgrade opportunities recommendation system 10 to analyze their (i.e. the customer's) imaging device install base to potentially (self-) identify beneficial imaging device and/or component upgrade(s). In such a case, the customer suitably contacts their sales representative at the vendor to further investigate such an upgrade recommendation.

In some embodiments, a particular set of ultrasound machines 16 are identified to evaluate new sales opportunities or imaging system equipment upgrade opportunities. These may represent one client 18, for example a hospital or department within a hospital, where one or more machines are identified. This defines the current install base (of ultrasound machines). In this instance each machine is taken in turn and each rule in the rule-base is run in turn.

The database 14 stores rules related to the replacement or upgrade of one of the devices 16. Each rule defines a set of conditions that identify a possible sales opportunity or a possible imaging system equipment upgrade opportunity. For example, a test may be that the efficiency of a system 16 is running during normal operation hours (e.g., at greater than 80%), or hospital scheduling data indicates the waiting list is too long (e.g. greater than 4 weeks), the machine is being overworked and procurement of a new machine is recommended to ease the workload. The corresponding workload of an existing machine or machines can therefore be divided between the existing machines and/or new machine(s). In an alternative articulation, the new machine may permit handling a larger workload, thereby providing increased revenue for the hospital. In another alternative articulation, the new machine may permit handling a larger workload, thereby providing the imaging service to a larger number of patients.

The system 10 also includes a computer or workstation or other electronic data processing device 20 operatively connected with the server computer 12. The computer 20 includes typical components, such as at least one electronic processor 22, at least one user input device (e.g., a mouse, a keyboard, a trackball, and/or the like) 24, and a display device 26. In some embodiments, the display device 26 can be a separate component from the computer 20. The workstation 20 is operatively connected to the database 14, and can also include one or more databases 28 (stored in a non-transitory storage medium such as RAM or ROM, a magnetic disk, an electronic medical record (EMR) database, a picture archiving and communication system (PACS) database, and the like).

In some embodiments, the database 14 also stores an installed base spreadsheet 32 that includes, for each installed medical imaging device, data including at least a device type, purchased components of the installed medical imaging device, available components (including software) for the installed medical imaging device 16, and an in-service date of the device, and so forth. The database 14 can also store an available devices spreadsheet 34 that includes, for each available medical imaging device, data including at least a device type and components available for the available medical imaging device.

Figure 2:
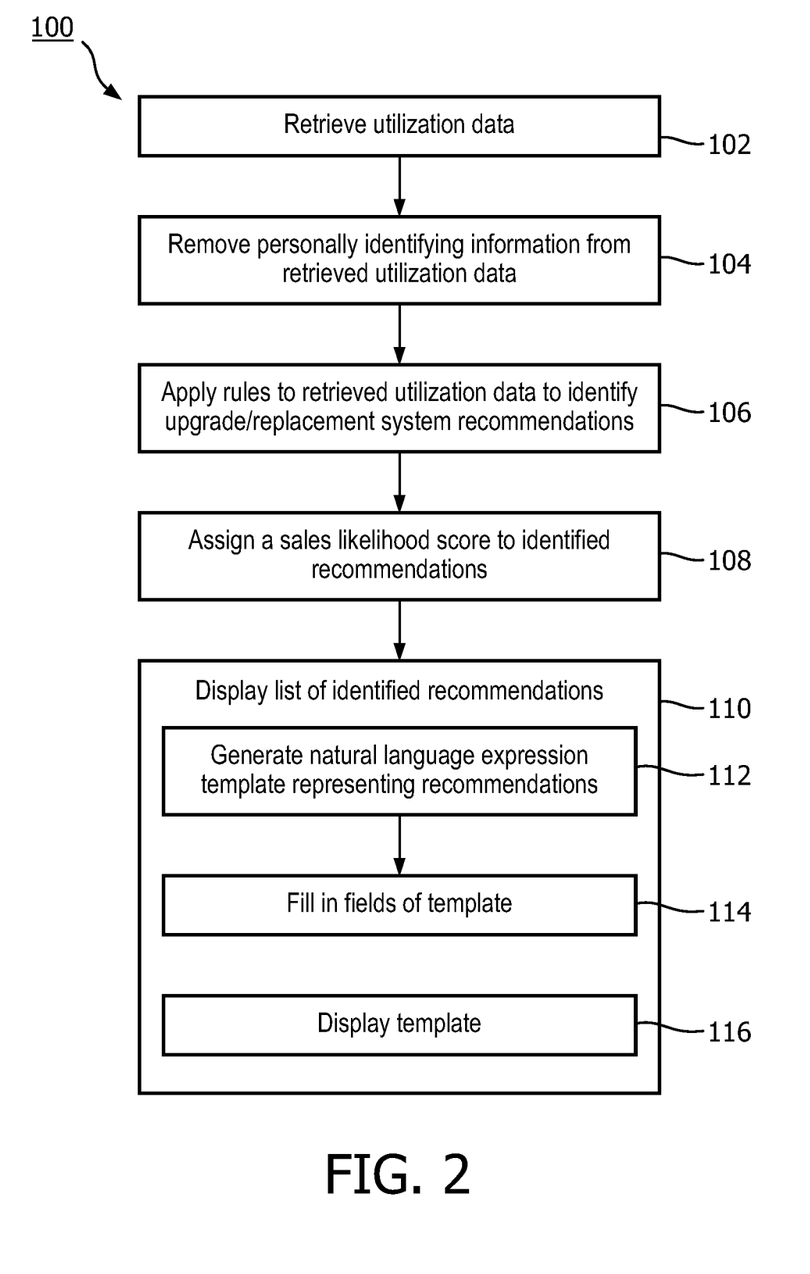
FIG. 2 shows an exemplary flow chart operation of the system of FIG. 1.

The at least one electronic processor 22 is operatively connected with a non-transitory storage medium (not shown) that stores instructions which are readable and executable by the at least one electronic processor 22 to perform disclosed operations including performing a method or process 100 for generating medical imaging device upgrade recommendations from utilization data. The non-transitory storage medium may, for example, comprise a hard disk drive, RAID, or other magnetic storage medium; a solid state drive, flash drive, electronically erasable read-only memory (EEROM) or other electronic memory; an optical disk or other optical storage; various combinations thereof; or so forth. In some examples, the method or process 100 may be performed by cloud processing. It should be noted that the processing workload of the upgrade opportunities recommendation system 10 may be variously divided between the server computer 12 and the workstation 20, for example the rules may be evaluated for a particular imaging device on the server 12 or on the workstation 20 depending upon the particular embodiment.

Moreover, while the illustrative user interfacing device is a workstation 20, in other embodiments the user interfacing device (i.e. "workstation") may be a mobile device such as a tablet computer, smart cellular telephone ("smartphone") or the like. Embodiments employing a mobile device have the benefit that they can be carried during customer site visits, so as to present the recommendations including the supporting utilization data directly to the customer. (See the example described later herein with reference to FIG. 4).

With reference to FIG. 2, an illustrative embodiment of the method 100 for generating medical imaging device upgrade recommendations from utilization data is diagrammatically shown as a flowchart. At 102, the at least one electronic processor 22 is programmed to retrieve, from the at least one database 14, utilization data 30 from logs of a plurality of installed medical imaging devices 16. The utilization data includes at least device efficiency, number of imaging sessions performed per month, components used during each scan, and an operation type, and so forth.

At 104, the at least one electronic processor 22 is programmed to remove personally identifying information (PII) from the retrieved utilization data 30. For example, the PII may be removed from the utilization data 30 by any suitable algorithm (e.g., a hashing algorithm). (In some embodiments, PII removal may be done at the time the machine logs, service logs, or other utilization data are uploaded to the server computer 12, in which case operation 104 may be omitted).

At 106, the at least one electronic processor 22 is programmed to apply a set of rules 29 to the utilization data 30 to identify one or more upgrade recommendations. Each upgrade recommendation includes (1) an identification of one or more of the installed medical imaging devices 16 or components of the installed medical imaging devices recommended to be upgraded or replaced, and (2) at least one of a replacement medical imaging device or component or a new medical imaging device or component for each of the installed medical imaging devices or components recommended to be upgraded or replaced. In some embodiments, the rules can be applied not only to the utilization data, but also applied to the retrieved installed base spreadsheet 32 and/or the retrieved available devices spreadsheet 34.

In some examples, the rules 29 include a rule for identifying an upgrade recommendation if the monetary cost of the upgrade is less than a forecast monetary revenue increase obtainable by the upgrade over a defined time horizon. In other examples, the rules 29 include a rule for identifying an upgrade recommendation if the monetary cost of the upgrade is less than a forecast monetary-equivalent value of increased medical diagnostic capability achieved by the upgrade.

In some embodiments, the at least one electronic processor 22 is programmed to generate machine-learned weights trained with sales and operation data to the utilization data. These weights can be applied to the utilization data 30 to identify the new or replacement imaging devices. In some examples, the weights can be based on regional factors (e.g., set at a regional level), since some rules or weights may only apply locally at select regional offices.

At 108, the at least one electronic processor 22 is programmed to assign a sales likelihood score 36 based on the identified upgrade recommendations. The score 26 is indicative of how likely an upgrade or replacement likelihood is implemented based on the application of the rules to the utilization data 30.

At 110, the at least one electronic processor 22 is programmed to display a list 38 of the at least one identified replacement or new medical imaging device or component. This display operation can include operations 112-116. At 112, the at least one electronic processor 22 is programmed to generate a natural language expression representing each upgrade recommendation. The natural language expression includes identification of: (1) the one or more installed medical imaging devices or components recommended to be upgraded or replaced, and (2) the at least one identified replacement or new medical imaging device, and a summary of utilization data on which the upgrade recommendation is based.

The summary of utilization data on which the upgrade recommendation is based includes at least one of: an increased revenue case indicating a cost of upgrade compared with a higher throughput compared with the installed medical imaging device; an additional services case indicating that the upgrade enables additional procedures not currently available with the installed medical imaging device or component; and a medical case indicated images showing an improved resolution attainable with the upgrade compared with the installed medical imaging device or component. The summary of utilization data can also include other parameters, including improved outcomes for patient satisfaction; improved clinician experience (e.g. scanning probe reduces repetitive strain injury), and so forth.

At 114, the at least one electronic processor 22 is programmed to fill in fields of the natural language expression template with the identification of the one or more installed medical imaging devices or components recommended to be upgraded or replaced, the at least one identified replacement or new medical imaging device, and the summary of utilization data on which the upgrade recommendation is based.

At 116, the at least one electronic processor 22 is programmed to display the natural language expression representing each upgrade recommendation as the list 38. The list 38 can be displayed on the display device 26 with the sales likelihood scores 36. In some examples, one or more graphs (not shown) (e.g., trend line graphs) showing a rising demand for scans from replacement or upgraded devices, which can indicate that a replacement or upgraded device is recommended.

Figure 3:
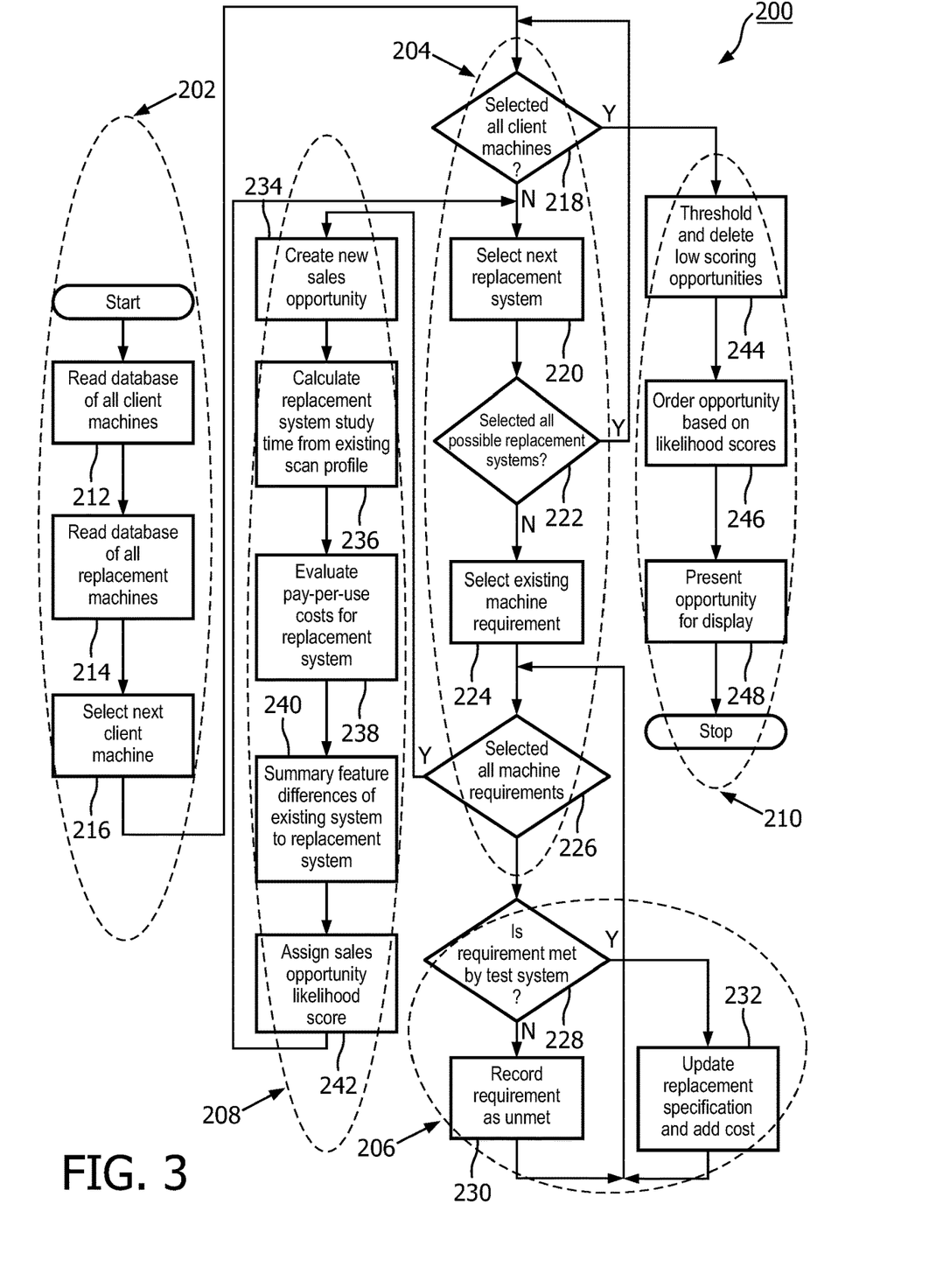
FIG. 3 shows another exemplary flow chart operation of the system of FIG. 1.

With reference to FIG. 3, an illustrative embodiment of another example embodiment of a method 200 for generating medical imaging device upgrade recommendations from utilization data is diagrammatically shown as a flowchart. The method 200 includes a retrieval operation 202, a selection operation 204, a requirement determination operation 206, a rules application operation 208, and a presentation operation 210.

The retrieval operation 202 includes operations 212-216. At 212, a database of all client machines is searched and read. At 214, a database of all replacement machines is searched and read. At 216, one of the client machines is selected. The retrieval operation 202 corresponds to the retrieval of the spreadsheets 32 and 34 from the database 14.

The selection operation 204 includes operations 218-226. At operation 218, it is determined whether all client machines have been selected. If so, then the method 200 proceeds to the presentation operation 210. If not, then the method 200 proceeds to operations 220-226. At 220, a next replacement system is selected. At 22, it is determined whether all possible replacement systems have been selected. If so, then the method 200 proceeds back to operation 218. If the method 200 proceeds to operation 224. At 224, an existing machine requirement is selected. At 226, it is determined whether or not all machine requirements have been selected. If so, then the method 200 proceeds to the requirement determination operation 206. If not, then the method 200 proceeds to the rules application operation 208.

The requirement determination operation 206 includes operations 228-232. At 228, it is determined whether the selected requirements are met by a test system. If so, then, at 230, the requirement is recorded as unmet. If so, then, at 232, the replacement specification of the machine requirement is updated, and a cost of the updated requirement is added. The client requirements can be divided into different classifications, including mandatory upgrades/replacements, preferred upgrades/replacements, and optional upgrades/replacements. The requirement classifications can be implemented as a sliding scale.

Once all machine requirements are selected at 226, the method 200 proceeds to the rules application operation 208, which includes operations 234-242. At 234, a new sales opportunity or a new imaging system equipment upgrade opportunity is created based on the selected machine requirements. At 236, a replacement system study is calculated from an existing scan profile. At 238, the pay-per-use costs for the proposed replacement system are evaluated. At 240, the feature differences between the existing imaging system and the replacement system are summarized. At 242, a sales opportunity or an imaging system equipment upgrade opportunity likelihood score is assigned to the sales opportunity or the imaging system equipment upgrade opportunity created at 234.

Once the scores are assigned, the method 200 proceeds back to operation 218. Once all client machines have been selected (i.e., have gone through operations 204-208), the method 200 proceeds to the presentation operation 210, which includes operations 244-248. At 244, the assigned scores are compared to a threshold, and any score below the threshold is deleted. At 246, the remaining scores are sorted into order by increasing likelihood scores. At 248, the sorted scores are formatted into a list and displayed for a user.

Figure 4:
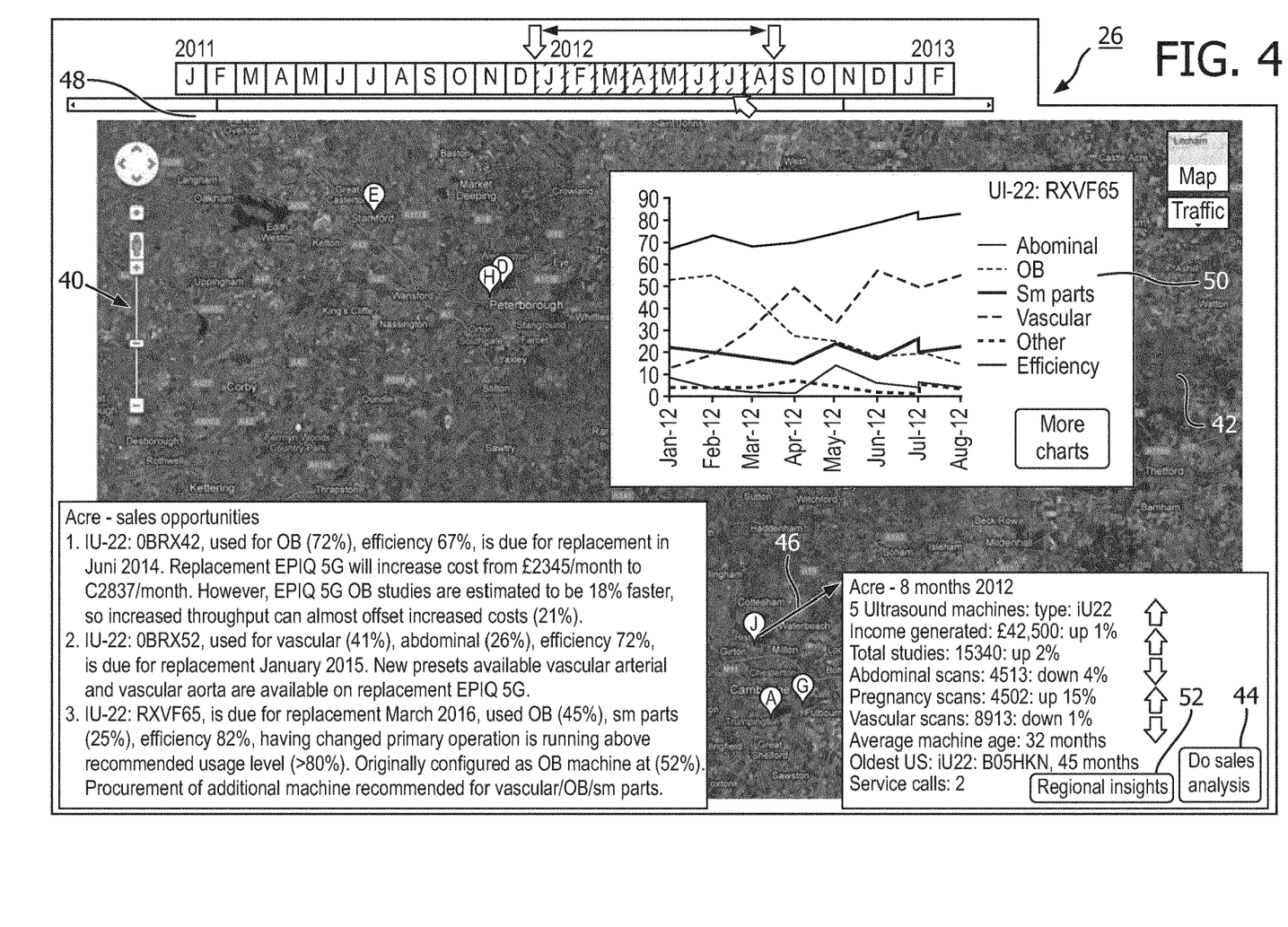
FIG. 4 shows an exemplary graphical user interface (GUI) of the system of FIG. 1.

FIG. 4 shows one contemplated embodiment of a user interface 40 of a sales tool. In this embodiment, the user interface 40 is linked to a mapping application (e.g., Google Maps) displayed on the display device 26 of the workstation 20 (which in this embodiment may, for example, optionally be a mobile device to facilitate sharing the displayed information to the customer during a site visit). As shown in FIG. 4, a map 42 shows positions of several client hospitals superimposed on a map. The map 42 can be scrollable and zoom-able via one or more user inputs. In this example, node "J" for Acre hospital can be selected, which brings up a summary of ultrasound machines supplied to that hospital. In the bottom right corner of the user interface 40, a button 44 labelled "do sales analysis" is selected which brings up sales opportunities or imaging system equipment upgrade opportunities for Acre hospital generated by the upgrade opportunity recommendation system 10. In addition, node "J" can be labeled with a time horizon setting 46 to bring up data at a time bar 48. The time horizon setting 46 includes data related to the date of sale, date of install, and the like of the machines at node J.

Sales opportunities or imaging system equipment upgrade opportunities can be expressed as statements that use client utilization data 30 to reinforce the justification for a sale. Several examples are shown in the bottom left corner of FIG. 4. The interface 40 also makes use of hyperlinks 50 to allow a sales representative to browse through the opportunities quickly, clicking on links to bring up related supporting information. For example, by selecting the hyperlink "RXVF65" of a sales opportunity or an imaging system equipment upgrade opportunity labelled "3" brings up a graph for the related system which illustrates the point "3" in the text that the primary operation mode for the device has changed. Optionally, if the presentation device 20 is a mobile device, this can be directly shared with the customer on-site by showing the customer the display 26.

The hyperlinks 48 provide easy functional access to more information hidden behind the information presented, allowing the user to select elements of interest and bring up more information on demand. For example, to select any given sales opportunity or a given imaging system equipment upgrade opportunity and to request the statistics, charts and further information that support a sales opportunity or an imaging system equipment upgrade opportunity, allowing the sales representative to present further justification for a sale based on the usage data of the relevant client machines proposed for replacement.

A profile is produced of the current utilization of each machine based on a significant number of operational months. The profile is a statistical model that represents the normal utilization of a client's machine based on using client recorded data. This allows the effect of utilization of alternative devices to be directly compared against the current client device to assess the advantages of changing devices.

In addition, the user interface 40 can include a regional insights button 52 that can bring up a window (not shown) that includes details related to the region of the selected node (e.g., node J). In addition, one or more areas of the map 42 can be selected to include multiple nodes, in which data from each node can be displayed.

In some embodiments, comparative data is used to demonstrate sales or upgrade opportunities. For example, the comparative data can comprise data from multiple hospitals (e.g., hospitals X and Y) (e.g. general hospitals in the public sector of the U.K.) in which hospital X has an MRI machine upgraded to a digital processing machine. Exams following the upgrade can typically be significantly reduced in time and the image quality can be improved. The investment in MRI machine by hospital X can then be assessed in terms of the payback time, or return on investment. A case could therefore be made for investing in the upgrade for hospital Y, since it is a similar hospital to X, and thus can be justified that it should improve patent throughput and diagnosis in the same way. In this case the relevance of the sales opportunity based on the direct comparison of peer hospitals can be used to enhance probability of a sale, improving its ranking score.

Figure 5:
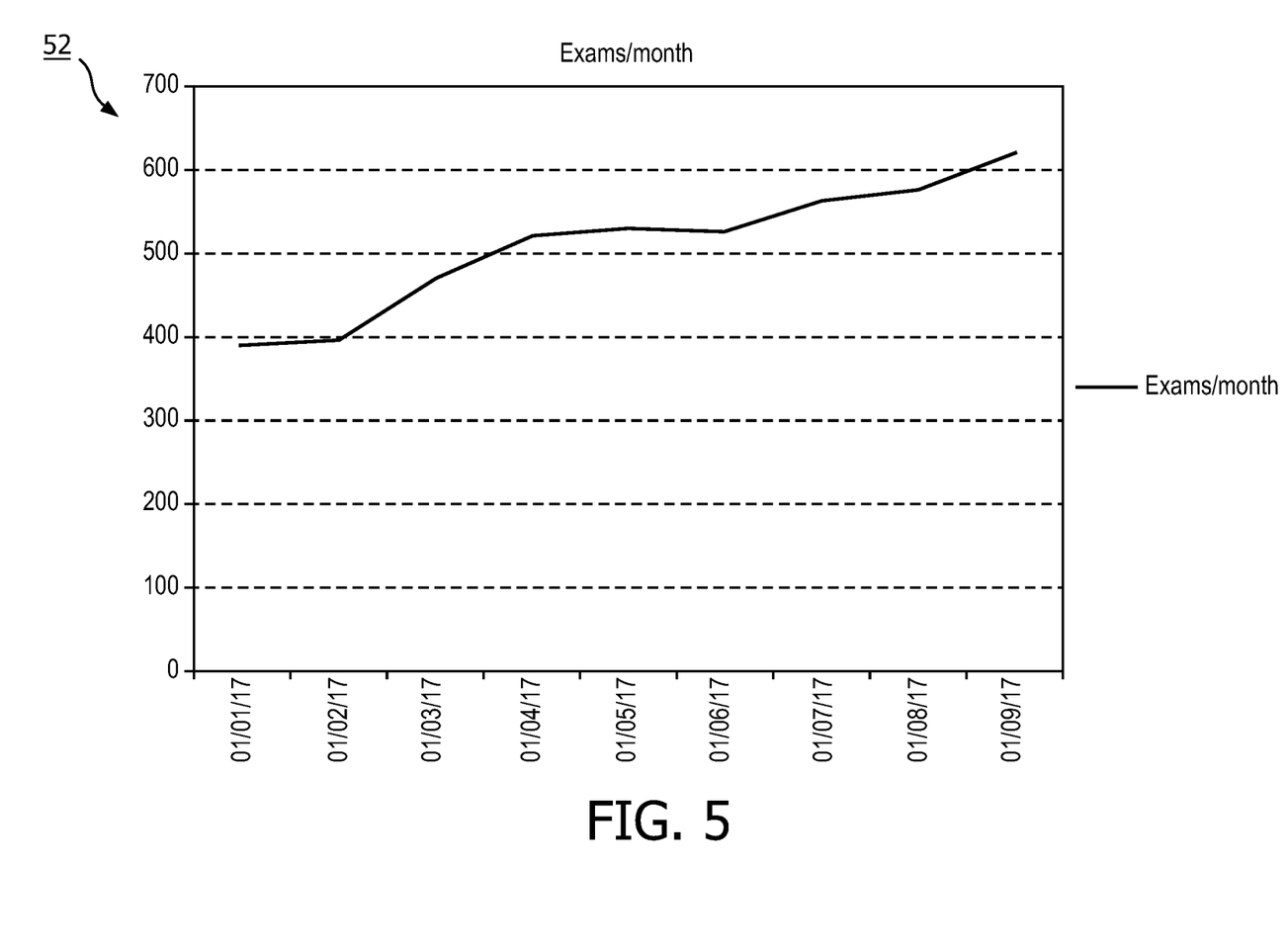
FIG. 5 shows a graph showing trend data indicative of a sale or upgrade opportunity.

In some embodiments, trend data is used to demonstrate sales or upgrade opportunities. FIG. 5 shows a trend graph 52 showing a steady growth in the monthly number of exams for an MRI machine over a period of time. Increasing throughput of patients may be enabled by various efficiency improvements, but the trend is such that there is an increasing case for the purchase of a new machine to spread the load of incoming patients. Further evidence may also be included such as the length of the waiting list and external information, such as local population figures and population growth estimates.

In some embodiments, sales or upgrade opportunities can be modeled over time. For example, these decisions can be large (particularly for larger equipment) and thus only made in certain intervals. Trade-offs over time should be looked at, (e.g. while a new PET and new MR both have advantages to a hospital, based on the use data, trend data, and budget data, it makes sense to purchase MR today and PET in 2 years).

In some embodiments, hospital trends, and thus needs of the hospital, are connected with a forecast of the vendor in future functionality. The trends and then tied together to roadmap sales or upgrade opportunities. This can greatly change the ranking of the opportunities. For example, a new MR machine purchase is planned for 2 years that would provide additional functionality to increase throughput or new procedure. In this regard, the above example might switch to show the opportunity is to buy a PET machine now and MR in two years. In addition to roadmaps, the forecast can also tie in clinical claims projected for a product, and perhaps more importantly reimbursement trends. For example, if there is a pending approval for CT for lung screening, a hospital may want to prepare for this in getting improve coverage, i.e. with an additional system, or with a system that facilitates lung screening (e.g. optimized for low dose).

The disclosure has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A non-transitory computer-readable medium storing instructions readable and executable by at least one computer to perform:
   a servicing support method including receiving logs from a plurality of installed medical imaging devices, hosting at least one database storing the logs of the plurality of installed medical imaging devices, and providing access to the logs stored in the at least one database by a servicing department for use in preventative and remedial servicing of the medical imaging devices; and
   an upgrade recommender method for presenting medical imaging device upgrade recommendations, the method comprising:
      retrieving utilization data quantifying medical imaging device utilization from the logs of the plurality of installed medical imaging devices stored in the at least one database;
      retrieving, for each installed medical imaging device, stored installed base data including at least a device type, purchased components of the installed medical imaging device, available components for the installed medical imaging device, and an in-service date of the installed medical imaging device;
      retrieving, for each available medical imaging device, stored available medical imaging device data including at least a device type and components available for the available medical imaging device;
      applying a set of rules to the utilization data and the installed base data and the available medical imaging device data to identify one or more upgrade recommendations wherein each upgrade recommendation comprises:
         an identification of one or more of the installed medical imaging devices or components of the installed medical imaging devices recommended to be upgraded or replaced; and
         an identification of at least one of a replacement medical imaging device or component or a new medical imaging device or component for each of the installed medical imaging devices or components recommended to be upgraded or replaced, wherein the upgrade recommendation is based on a basis including at least one of:
            an increased revenue case indicating a cost of upgrade compared with a higher throughput compared with the installed medical imaging device;
            an additional services case indicating that the upgrade enables additional procedures not currently available with the installed medical imaging device or component; and/or
            a medical case indicated by images showing an improved resolution attainable with the upgrade compared with the installed medical imaging device or component;
      generating a natural language expression representing each upgrade recommendation wherein the natural language expression includes identification of the one or more installed medical imaging devices or components recommended to be upgraded or replaced and of the at least one identified replacement or new medical imaging device, and further includes a summary of the utilization data retrieved from the logs of the plurality of installed medical imaging devices stored in the at least one database on which the upgrade recommendation is based; and
      displaying, on a graphical user interface (GUI) presented on a display device, a list of the at least one upgrade recommendation including displaying, for each upgrade recommendation, the natural language expression representing the upgrade representation.

2. The non-transitory computer-readable medium of claim 1, wherein the generating comprises:
   filling in fields of a natural language expression template with the identification of the one or more installed medical imaging devices or components recommended to be upgraded or replaced, the at least one identified replacement or new medical imaging device, and the summary of utilization data on which the upgrade recommendation is based.

3. The non-transitory computer-readable medium of claim 1, wherein the summary of utilization data on which the upgrade recommendation is based includes:
an increased revenue case indicating a cost of upgrade compared with a higher throughput compared with the installed medical imaging device;
an additional services case indicating that the upgrade enables additional procedures not currently available with the installed medical imaging device or component; and
a medical case indicated by images showing an improved resolution attainable with the upgrade compared with the installed medical imaging device or component.

4. The non-transitory computer-readable medium of claim 3, wherein the rules include a rule for identifying an upgrade recommendation if the monetary cost of the upgrade is less than a forecast monetary revenue increase obtainable by the upgrade over a defined time horizon.

5. The non-transitory computer-readable medium of claim 3, wherein the rules include a rule for identifying an upgrade recommendation if the monetary cost of the upgrade is less than a forecast monetary-equivalent value of increased medical diagnostic capability achieved by the upgrade.

6. The non-transitory computer-readable medium of claim 1, wherein the upgrade recommender method further includes:
removing personally identifying information from the retrieved utilization data.

7. The non-transitory computer-readable medium of claim 1, wherein the utilization data includes device efficiency, number of imaging sessions performed per month, components used during each scan, and an operation type.

8. The non-transitory computer-readable medium of claim 1, wherein the applying includes:
generating machine-learned weights trained with sales and operation data to the utilization data; and
applying the weights to the utilization data to identify the new or replacement imaging devices.

9. The non-transitory computer-readable medium of claim 1, wherein the rules of the set of rules are assigned weights, and the upgrade recommender method further includes:
assigning a score to the identified upgrade recommendations using the weights, the score being indicative of a likelihood that the upgrade recommendation is implemented; and
adjusting the weights assigned to the rules of the sets of rules based on success or failure of the at least one upgrade recommendation.

10. The non-transitory storage medium of claim 1, wherein each upgrade recommendation is associated with one or more of an upgraded image quality or upgraded image processing speed that is different than one or more of an installed image quality or installed image processing speed associated with the installed medical imaging devices.

11. The non-transitory storage medium of claim 10, wherein the upgrade recommender method further includes, responsive to at least one user input to the GUI, at least one of:
displaying a location of one or more installed medical imaging devices for which the at least one upgrade recommendation is generated;
displaying a sales analysis for each upgrade recommendation;
displaying a time line related to sales and installation data of one or more installed medical imaging devices at a selected location; and
displaying one or more hyperlinks selectable by a user to display additional information related to the at least one upgrade recommendation.

12. An upgrade opportunity recommendation operating in conjunction with a server that receives logs from a plurality of installed medical imaging devices, hosts at least one database storing the logs of the plurality of installed medical imaging devices, and provides access to the logs stored in the at least one database by a servicing department for use in preventative and remedial servicing of the medical imaging devices, the system comprising:
a mobile device including a display device configured to present a sales pitch;
at least one electronic processor programmed to:
retrieve utilization data from the logs of the plurality of installed medical imaging devices stored at the at least one database hosted by the server;
apply a set of rules to the utilization data to identify one or more upgrade recommendations wherein each upgrade recommendation comprises an identification of one or more of the installed medical imaging devices or components of the installed medical imaging devices recommended to be upgraded or replaced and at least one of a replacement medical imaging device or component or a new medical imaging device or component for each of the installed medical imaging devices or components recommended to be upgraded or replaced, wherein the upgrade recommendation is based on at least one of:
an increased revenue case indicating a cost of upgrade compared with a higher throughput compared with the installed medical imaging device,
an additional services case indicating that the upgrade enables additional procedures not currently available with the installed medical imaging device or component, and
a medical case indicated by images showing an improved resolution attainable with the upgrade compared with the installed medical imaging device or component; and
generate a natural language expression representing each upgrade recommendation wherein the natural language expression includes identification of the one or more installed medical imaging devices or components recommended to be upgraded or replaced and of the at least one identified replacement or new medical imaging device, and further includes a summary of utilization data on which the upgrade recommendation is based;
wherein the mobile device is configured to present the sales pitch by displaying the generated natural language expression representing each upgrade recommendation.

13. The system of claim 12, wherein the at least one electronic processor is programmed to generate the natural language expression by:
filling in fields of a natural language expression template with the identification of the one or more installed medical imaging devices or components recommended to be upgraded or replaced, the at least one identified replacement or new medical imaging device, and the summary of utilization data on which the upgrade recommendation is based.

14. The system of claim 13, wherein the summary of utilization data on which the upgrade recommendation is based includes at least one of:
- an additional services case indicating that the upgrade enables additional procedures not currently available with the installed medical imaging device or component; and
- a medical case indicated by images showing an improved resolution attainable with the upgrade compared with the installed medical imaging device or component.

15. The system of claim 14, wherein the rules include at least:
- a rule for identifying an upgrade recommendation if the monetary cost of the upgrade is less than a forecast monetary revenue increase obtainable by the upgrade over a defined time horizon; and
- a rule for identifying an upgrade recommendation if the monetary cost of the upgrade is less than a forecast monetary-equivalent value of increased medical diagnostic capability achieved by the upgrade.

16. The system of any claim 12, wherein the at least one database is further configured to store:
- an installed base spreadsheet that includes, for each installed medical imaging device, data including at least a device type, purchased components of the installed medical imaging device, available components for the installed medical imaging device, and an in-service date of the device; and an available devices spreadsheet that includes, for each available medical imaging device, data including at least a device type and components available for the available medical imaging device;
- wherein the at least one electronic processor is further programmed to apply the set of rules to data retrieved from the installed base and available devices spreadsheets.

17. The system of claim 12, wherein the at least one electronic processor is further programmed to:
- assign a score to the identified upgrade recommendations, the score being indicative of a likelihood that the upgrade recommendation is implemented.

18. A non-transitory computer-readable medium storing instructions readable and executable by a workstation including at least one electronic processor to perform operations to generate medical imaging device upgrade recommendations from utilization data, the instructions comprising operations to:
- retrieve, from at least one database, utilization data from logs of a plurality of installed medical imaging devices;
- apply a set of rules to the utilization data to identify one or more upgrade recommendations wherein each upgrade recommendation comprises:
  - an identification of one or more of the installed medical imaging devices or components of the installed medical imaging devices recommended to be upgraded or replaced; and
  - at least one of a replacement medical imaging device or component or a new medical imaging device or component for each of the installed medical imaging devices or components recommended to be upgraded or replaced, wherein the upgrade recommendation is associated with one or more of an upgraded image quality or upgraded image processing speed that is different than one or more of an installed image quality or installed image processing speed associated with the installed medical imaging devices; and
- display, on a display device, a list of the at least one identified replacement or new medical imaging device or component by operations including:
  - generating a natural language expression to represent each upgrade recommendation wherein the natural language expression includes identification of the one or more installed medical imaging devices or components recommended to be upgraded or replaced and of the at least one identified replacement or new medical imaging device, and a summary of utilization data on which the upgrade recommendation is based;
  - ranking each upgrade recommendation based on an identified improvement to the medical imaging device; and
  - displaying a list of the ranked upgrade recommendations.

19. The non-transitory computer-readable medium of claim 18, wherein the rules include at least:
- a rule to identify an upgrade recommendation if the monetary cost of the upgrade is less than a forecast monetary revenue increase obtainable by the upgrade over a defined time horizon; and
- a rule to identify an upgrade recommendation if the monetary cost of the upgrade is less than a forecast monetary-equivalent value of increased medical diagnostic capability achieved by the upgrade.

20. The non-transitory computer-readable medium of claim 18, further storing:
- an installed base spreadsheet that includes, for each installed medical imaging device, data including at least a device type, purchased components of the installed medical imaging device, available components for the installed medical imaging device, and an in-service date of the device; and
- an available devices spreadsheet that includes, for each available medical imaging device, data including at least a device type and components available for the available medical imaging device;
- wherein the operation to apply the set of rules includes application of the rules to data retrieved from the installed base and available devices spreadsheets.

* * * * *